(12) United States Patent
Ukon et al.

(10) Patent No.: US 8,704,174 B2
(45) Date of Patent: Apr. 22, 2014

(54) REFINED OIL DEGRADATION LEVEL MEASURING INSTRUMENT AND REFINED OIL DEGRADATION LEVEL MEASURING METHOD

(75) Inventors: Juichiro Ukon, Kyoto (JP); Toshiyuki Tsujimoto, Kyoto (JP)

(73) Assignee: Horiba, Ltd., Kyoto (JP)

( * ) Notice: Subject to any disclaimer, the term of this patent is extended or adjusted under 35 U.S.C. 154(b) by 357 days.

(21) Appl. No.: 12/976,848

(22) Filed: Dec. 22, 2010

(65) Prior Publication Data

US 2011/0155925 A1 Jun. 30, 2011

(30) Foreign Application Priority Data

Dec. 24, 2009 (JP) ................................. 2009-293535

(51) Int. Cl.
G01N 33/28 (2006.01)
(52) U.S. Cl.
CPC ................................. G01N 33/2888 (2013.01)
USPC ........................................................ 250/301
(58) Field of Classification Search
CPC ........................ G01N 33/2888; G01N 33/2876
USPC ........................................................ 250/301
See application file for complete search history.

(56) References Cited

U.S. PATENT DOCUMENTS

| | | | |
|---|---|---|---|
| 4,716,363 A | 12/1987 | Dukes et al. | |
| 4,814,614 A | 3/1989 | Tsui | |
| 6,633,043 B2 | 10/2003 | Hegazi et al. | |
| 7,136,155 B2 * | 11/2006 | Kong et al. | ........................ 356/70 |
| 2003/0141459 A1 | 7/2003 | Hegazi et al. | |
| 2007/0187617 A1 | 8/2007 | Kong et al. | |
| 2009/0189074 A1 | 7/2009 | Bello | |

FOREIGN PATENT DOCUMENTS

| | | |
|---|---|---|
| JP | 63-308596 | 12/1988 |
| JP | 06-074900 | 3/1994 |
| JP | 2005-536715 | 12/2005 |
| JP | 2006-242595 | 9/2006 |
| WO | 03/073075 | 9/2003 |
| WO | 2009/080049 | 7/2009 |

OTHER PUBLICATIONS

Sami D. Alaruri, M. Rasas, Ossama Alamedine, S. Jubian, F. Al-Bahrani, M. Quinn, "Remote characterization of crude and refined oils using a laser fluorosensor system." Optical Engineering, vol. 34, No. 1 (Jan. 1995) pp. 214-221. Downloaded Feb. 13, 2013. <doi: 10.1117/12.188308>.*

(Continued)

Primary Examiner — Constantine Hannaher

(57) ABSTRACT

In situ monitoring of a degradation level of refined oil during use is provided. An excitation light irradiation unit varies intensity of excitation light to irradiate the excitation light onto the refined oil with a resulting fluorescence. A fluorescence intensity detection unit detects the intensity of fluorescence generated by the irradiation of the excitation light, and a time lag characteristic calculation unit calculates a time lag characteristic of a fluorescence intensity variation with respect to the intensity variation of the excitation light. A degradation index value acquisition unit provides to a predetermined correlation between a degradation index value indicating a degradation level of the refined oil and the time lag characteristic is used to acquire a degradation index value from a time lag characteristic calculated in the time lag characteristic calculation unit to determine the current degradation status of the oil.

12 Claims, 4 Drawing Sheets

FIG. 1

(56) References Cited

OTHER PUBLICATIONS

Markova, L.V. et al., "Fluorescence Sensor for Characterization of Hydraulic Oil Degradation", Tribology in Industry, vol. 29, No. 1&2, 2007, pp. 33-36.

Vanhanen, Jarmo et al., "Characterization of Used Mineral Oil Condition by Spectroscopic Techniques", Applied Optics, vol. 43, No. 24, Aug. 20, 2004, pp. 4718-4722.

European Application No. 10015983.9 Extended Search Report dated Nov. 17, 2011, 9 pages.

Dolenko, Tatiana A. et al., "Fluorescence Diagnostics of Oil Pollution in Coastal Marine Waters by Use of Artificial Neural Networks", Applied Optics, vol. 41, No. 24, Aug. 20, 2002, pp. 5155-5166.

Endo, Yasushi et al., "Evaluation of Oxidative Deterioration of Lipid in Dried Foods Using the Solid Sample Fluorescence Spectrophotometry", Nippon Shokuhin Kogyo Gakkaisishi, vol. 40, No. 3, pp. 176-180, 1993.

* cited by examiner

REFINED OIL DEGRADATION LEVEL MEASURING INSTRUMENT AND REFINED OIL DEGRADATION LEVEL MEASURING METHOD

BACKGROUND OF THE INVENTION

1. Field of the Invention

The present invention relates to a refined oil degradation level measuring instrument and a refined oil degradation level measuring method that can measure a degradation level of refined oil represented by lubricant oil or insulating oil for an internal combustion engine or the like when mounted in a ship or a car, food oil, or the like.

2. Description of Related Art

Refined oil refers to base oil mixed with an additive such as an antioxidant or detergent dispersant, and as the types thereof, as described above, there are lubricant oil used for the purposes of friction reduction, heat radiation, and the like, insulating oil used for a transformer, food oil, and the like. Such refined oil gradually degrades with use and time. As an index indicating a level of the degradation, a neutralization number, a total acid number, a total base number, or the like that is a state quantity of the additive has conventionally been used.

For example, the total base number is an index indicating acid neutralization performance, cleanliness, and the like of the additive, and a reduction of a value thereof indicates that consumption of the additive progresses.

For now, as a method that is intended to measure the total base number and set in a standard, there are a titration method that determines an endpoint when a volumetric solution reaches a constant pH (JIS) and a method that makes a determination on the basis of an FTIR absorbance (ASTM).

CITATION LIST

Patent Literature

Patent literature 1: U.S. Pat. No. 6,633,043 B2

SUMMARY OF THE INVENTION

Technical Problem

However, the above-described measuring methods should sample refined oil to perform batch processing, and the former requires high expertise for the measurement whereas the latter has a disadvantage of being susceptible to vibration, so that it is difficult to make measurements on site where the refined oil is used, i.e., difficult to make in-situ measurements.

As a result of having made an intensive study to solve such a problem, the present inventor has found that there is a strong correlation between a time lag of fluorescence generated when excitation light having a constant wavelength is irradiated on refined oil and a degradation index value of the refined oil. The present invention is adapted to measure a degradation level of the refined oil on the basis of the correlation, and a main object thereof is to enable the degradation level to be easily measured on site where the refined oil is used (in situ).

Note that as a literature disclosing a method that uses fluorescence to measure the type and degradation level of refined oil, there is Patent literature 1. However, the method described in Patent literature 1 is, in short, adapted to represent an intensity time variation profile for each fluorescence wavelength as a contour indicating the same intensity on a graph having a horizontal axis representing time and a vertical axis representing a wavelength, and determine the type and degradation level of the oil on the basis of similarity of the contour diagram. That is, in Patent literature 1, the relative similarity in time variation profile among respective fluorescence wavelengths is used, but a time lag characteristic in the generation of fluorescence with respect to excitation light irradiation is not focused on at all. In addition, Patent literature 1 does not describe or suggest the presence of the correlation between the time lag characteristic and the degradation index value of refined oil. Therefore, it can be said that Patent literature 1 and the present invention have similar features but are not the same.

Solution to Problem

That is, a refined oil degradation level measuring instrument or a refined oil degradation level measuring method is adapted to: vary an intensity of excitation light to irradiate the excitation light on refined oil that is a measurement object; detect an intensity of fluorescence generated in the refined oil irradiated with the excitation light; calculate a time lag characteristic of a fluorescence intensity variation with respect to the intensity variation of the excitation light; and refer to a correlation between a degradation index value indicating a degradation level of the refined oil and the time lag characteristic, which are preliminarily acquired by measurements or the like, to acquire the degradation index value from the time lag characteristic calculated in the above manner.

If so, it is only necessary to irradiate excitation light on refined oil, and receive fluorescence to perform calculation processing, and therefore, for example, by attaching the refined oil degradation level measuring instrument to a car, ship, or the like, a degradation level of the refined oil in use can be monitored without sampling the refined oil.

As a specific degradation index, a total base number can be cited.

Advantageous Effects of Invention

According to the present invention configured as described above, for example, by providing in an oil tank a window that transmits an irradiating excitation light onto refined oil inside the oil tank, whereby fluorescence from the excited refined oil is detected to automatically calculate a degradation level, and therefore no particular expertise is required for the measurement operation. Also, no vulnerability to vibration or contamination is found, and therefore the degradation level of the refined oil can be measured in situ, and further monitored in real time without a separate sampling of the refined oil.

As a result, the refined oil can be monitored and changed at an appropriate timing, so that not only a mechanical device failure, reduction in operating efficiency, or the like due to erroneously delayed change of the refine oil can be prevented, but unnecessary waste due to too frequent a change of the refined oil can be prevented, which can also contribute to ECO.

A refined oil degradation level measuring instrument includes an excitation light irradiation unit that varies an intensity of excitation light to irradiate the excitation light on refined oil that is a measurement object, a fluorescence intensity detection unit that detects an intensity of fluorescence that is generated in the refined oil irradiated with the excitation light, a time lag characteristic calculation unit that calculates a time lag characteristic of a fluorescence intensity variation with respect to the intensity variation of the excitation light, a correlation storage unit that preliminarily stores a correlation between a degradation index value indicating a degradation level of the refined oil and the time lag characteristic, and a degradation index value acquisition unit that refers to the correlation to acquire the degradation index value from the time lag characteristic calculated in the time lag characteristic calculation unit, wherein the degradation index is a total base number.

An oil degradation level measuring instrument to determine a current status degradation of lubricating oil being used in an internal combustion engine includes a measurement quantity of lubrication oil contained within a lubrication system of the internal combustion engine, a source of excitation light of an intensity such as a UV laser or another form of light to where the intensity and quantity of light energy in the form of photons can raise the vibration status of the oil specimen to an excited level and when the oil specimen drops down to a ground state it releases a characteristic different frequency of light. The wavelength of light excites the measurement quantity of lubrication oil into a state of fluorescence. A detection unit measures an intensity of fluorescence light over a predetermined time period from the application of excitation light onto the quantity of lubrication oil. A time lag characteristic calculation unit calculates a time lag characteristic of a predetermined fluorescence intensity variation with respect to the application of the excitation light.

A correlation storage unit stores a correlation between a degradation index value indicating a degradation level of the refined oil and the time lag characteristic. A degradation index value acquisition unit refers to the stored correlation to acquire the degradation index value from the time lag characteristic calculated in the time lag characteristic calculation unit, and an output member indicates a status signal representative of the current degradation status of the lubricating oil in the internal combustion engine.

A refined oil degradation level measuring method includes an excitation light irradiation step of varying an intensity of excitation light to irradiate the excitation light on refined oil that is a measurement object, a fluorescence intensity detection step of detecting an intensity of fluorescence that is generated in the refined oil irradiated with the excitation light, a time lag characteristic calculation step of calculating a time lag characteristic of a fluorescence intensity variation with respect to the intensity variation of the excitation light; and a degradation index value acquisition step of referring to a preliminarily acquired correlation between a degradation index value indicating a degradation level of the refined oil and the time lag characteristic to acquire the degradation index value from the time lag characteristic calculated in the time lag characteristic calculation step.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

In the following, an embodiment of the present invention is described with reference to the drawings.

Figure 1:
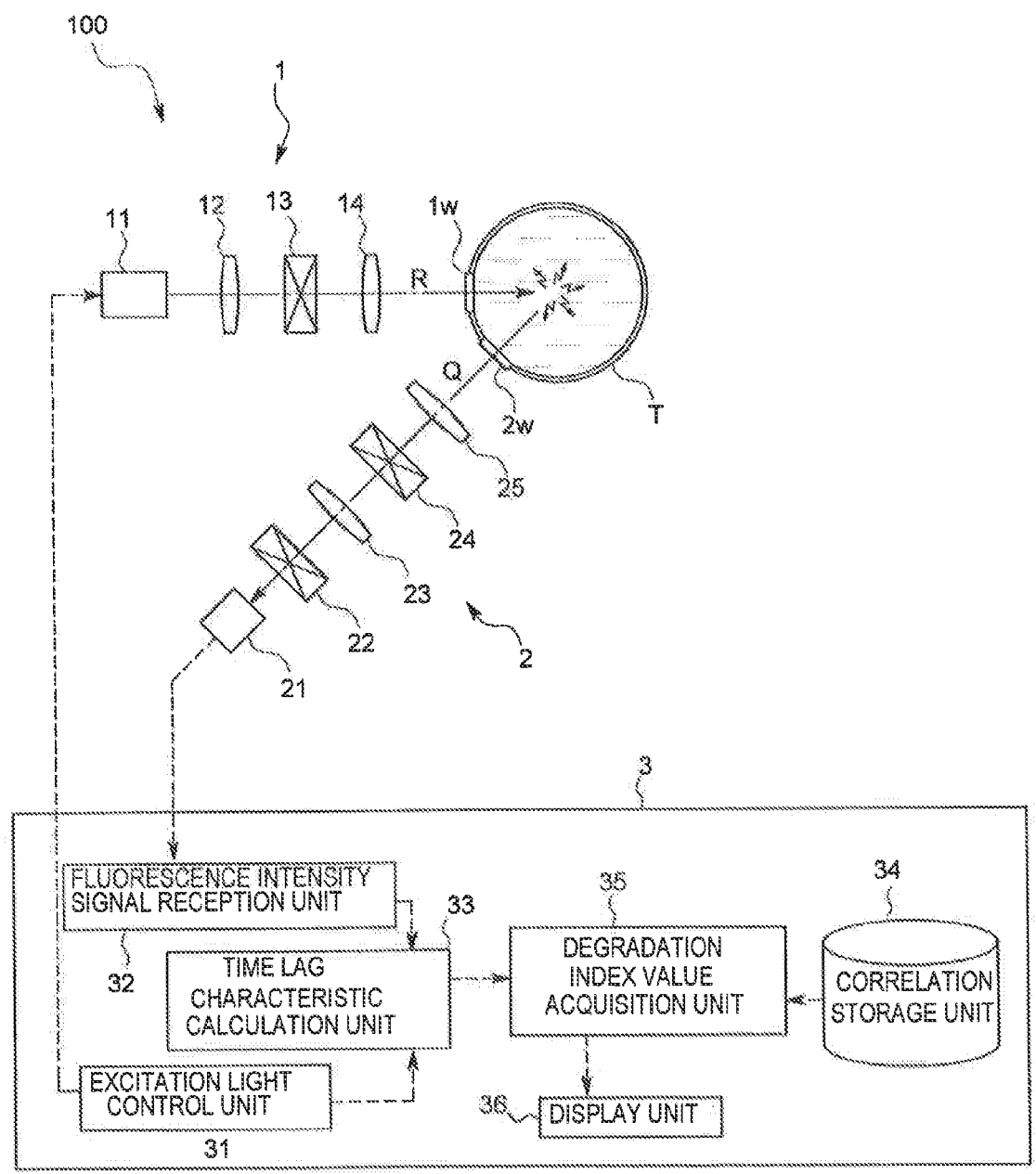
FIG. 1 is an overall schematic diagram of a refined oil degradation level measuring instrument in one embodiment of the present invention.

A refined oil degradation level measuring instrument 100 according to the present embodiment is, as illustrated in FIG. 1, an instrument that, for example, irradiates excitation light R on lubricant oil, which can be contained in an oil tank T of an internal combustion engine and one type of refined oil, and uses fluorescence Q generated by the irradiation to measure a degradation level of the lubricant oil.

To provide a more specific description, the refined oil degradation level measuring instrument 100 is provided with: an excitation light irradiation unit 1 that irradiates the excitation light R to a desired intensity to enable fluorescence light from the lubricant and a fluorescence intensity detection unit 2 that detects a resultant intensity of the fluorescence Q generated in the lubricant oil; and a calculation device 3 that, on the basis of the fluorescence intensity detected in the fluorescence intensity detection unit 2, determines the degradation level of the lubricant oil.

The excitation light irradiation unit 1 includes, in the present embodiment, a laser light source 11 that generates near ultraviolet light of 360 nm, a band pass filter 13 that limits a wavelength band of the ultraviolet light to a narrow band to make it serve as the excitation light R, and a collimator lens 12 and collecting lens 14 that are provided in appropriate positions. As for a laser light source 11 that generates the near ultraviolet light, within a range of 350-380 nm is preferable. The excitation light R generated in the excitation light irradiation unit 1 can be irradiated on the internal lubricant oil through, for example, an excitation light inlet window 1w provided in the oil tank T.

The fluorescence intensity detection unit 2 is one provided with: a low pass filter 24 that can pass the fluorescence Q having a longer wavelength band than a predetermined wavelength of fluorescence light that is generated in the lubricant oil by the irradiation of the excitation light R and comes out through a fluorescence outlet window 2w provided in the oil tank T; a spectroscope 22 that extracts the fluorescence light having a desired wavelength out of the fluorescence Q passing through the low pass filter 24; an optical sensor 21 such as a CCD that receives the fluorescence Q extracted by the spectroscope 22 to measure an intensity of the fluorescence Q; and a collecting lens 23 and a collimator lens 25 that are provided in appropriate optical positions. A wavelength of the fluorescence Q to be measured is set within a wavelength band different from that of the excitation light R to prevent any possible cross talk, and the present embodiment is adapted to measure the fluorescence Q, for example, 420 nm, preferably within a range of 400-600 nm.

The calculation device 3 includes: a digital circuit having a CPU, memory unit, and the like and an analog circuit having an amplifier that drives the laser light source 11, or other light sources, and on the basis of the collaboration between them, fulfills functions as an excitation light control unit 31, a fluorescence intensity signal reception unit 32, a time lag characteristic calculation unit 33, a correlation storage unit 34, a degradation index value acquisition unit 35, a display unit 36, and the like.

The excitation light control unit 31 can output a control signal to the laser light source 11 to vary an intensity of the excitation light R. In the present embodiment, the excitation light control unit 31 outputs a control signal to generate an excitation light R having, for example, a very short pulsed shape. Note that representative examples of the intensity variation include an aspect in which in addition to ON/OFF as in the present embodiment, the intensity is varied in a sine or triangle wave pattern.

The fluorescence intensity signal reception unit 32 can receive a fluorescence intensity signal outputted from the optical sensor 21.

The time lag characteristic calculation unit 33 can calculate a time lag characteristic of a fluorescence intensity variation indicated by the fluorescence intensity signal with respect to the intensity variation of the excitation light R. More specifically, as described above, short pulsed light is outputted as the excitation light R, and therefore rise time of the pulse, for example, output time of the control signal can be used as a reference point or signal to calculate a time lag characteristic that is a period of time from the reference time to a time point when a peak value of the fluorescence intensity is reduced to a value having a predetermined ratio with respect to is the peak value (hereinafter also referred to as a lag time).

Figure 2:
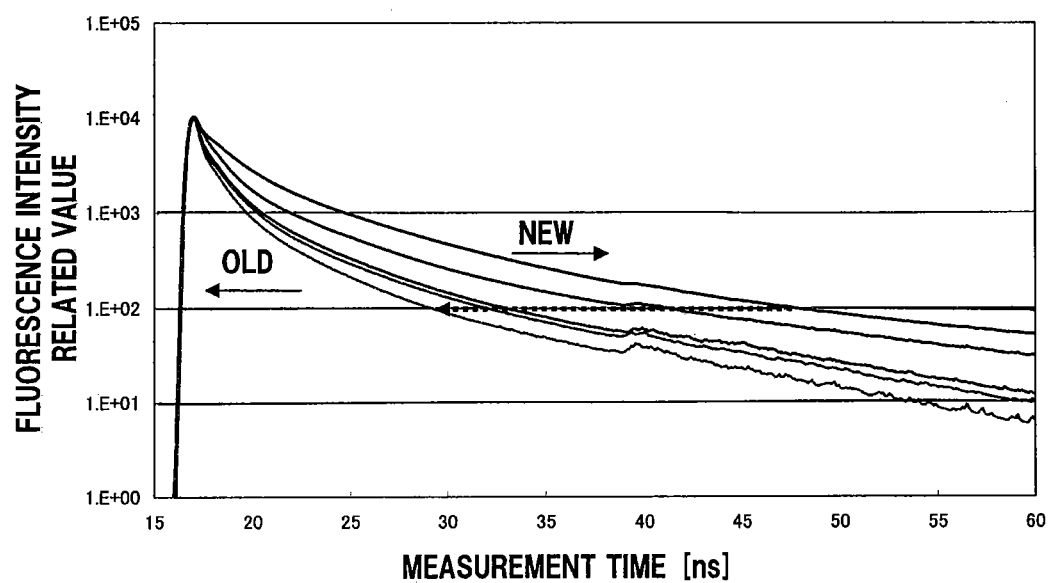
FIG. 2 is a diagram of measurement results illustrating differences in time variation profile of fluorescence intensity due to differences among new and old refined oils.

The correlation storage unit 34 is set in a predetermined area of the memory, to preliminarily store a correlation between a predetermined total base number representative of the type of lubricant oil and the time lag characteristic. The correlation is one that has been found as a result of intensive effort by the present inventors. To describe an example of the correlation, for example, in the case of providing a short pulsed excitation light R as described above, a time variation profile of the fluorescence intensity (in practice, a relevant value corresponding to the fluorescence intensity) varies along with a time lag as illustrated in FIG. 2. If this is compared among a new lubricant oil and respective lubricant oils of the same type that have been gradually degraded, it turns out that the period of time from the reference time to the time point when the peak value of the fluorescence intensity is reduced to the value having the predetermined ratio with respect to the peak value gradually decreases. Note that, in practice, absolute values of fluorescence intensities of the respective lubricant oils are different from one another; however, in FIG. 2, in order to facilitate understanding, known normalization calculations are applied to make peak values of the respective fluorescence intensities equal to one another.

Figure 3:
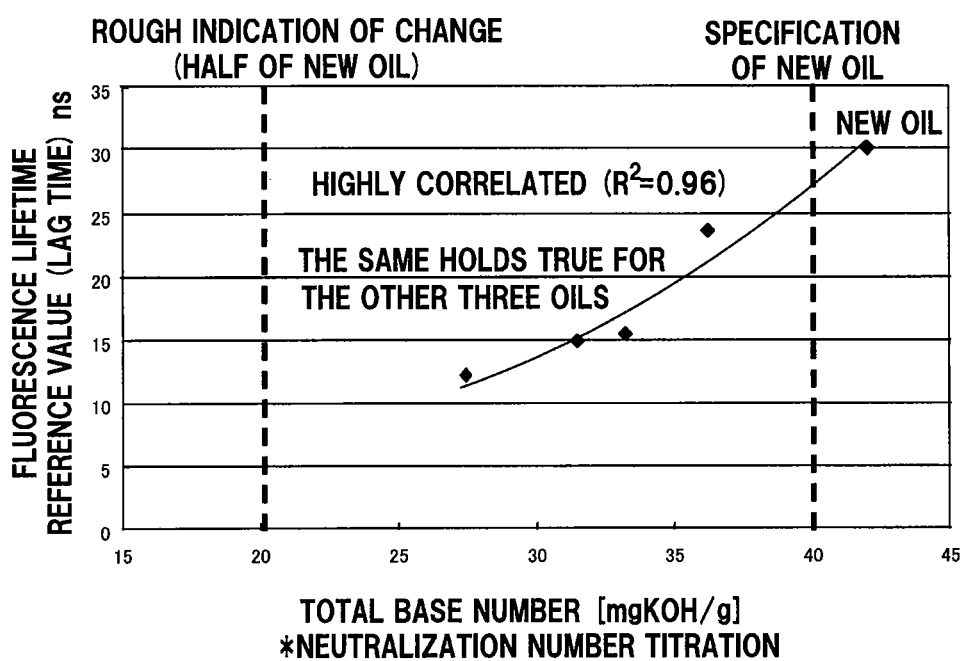
FIG. 3 is a calibration curve diagram illustrating a correlation between a total base number and a time lag characteristic.

Also, as a result of examining a relationship between the total base number measured by a known titration method set in the standard and the lag time, as illustrated in FIG. 3, it was discovered that the relationship was highly correlated. The correlation, in other words, a calibration curve is stored by the correlation storage unit 34. The degradation index value acquisition unit 35 is one that refers to the correlation stored in the correlation storage unit 34 to acquire, from the lag time calculated in the time lag characteristic calculation unit 33, the total base value serving as the degradation index value.

The display unit 36 displays the total base number acquired in the degradation index value acquisition unit 35 or a signal representative thereof. In addition, the display unit 36 may display an oil degradation level in multiple stages on the basis of the total base number, or may determine on the basis of the total base number whether or not the oil should be changed and display a result of such determination to the user.

Figure 4:
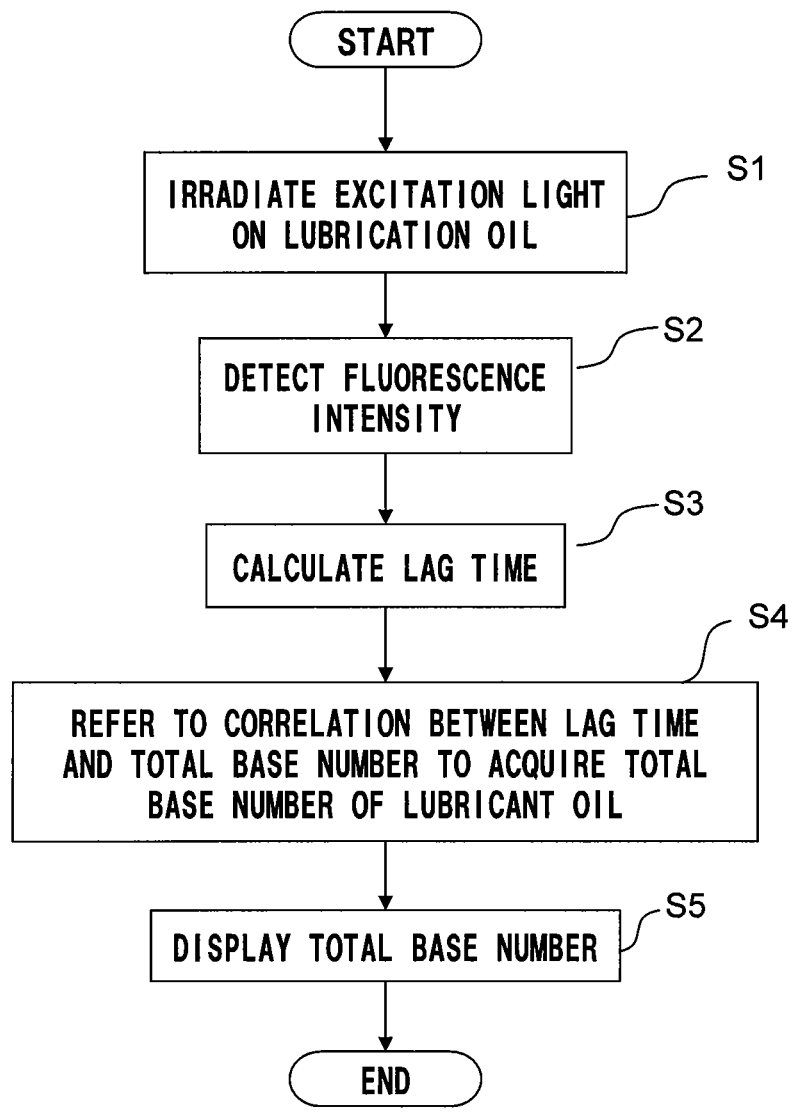
FIG. 4 is an operational flowchart of the refined oil degradation level measuring instrument in the one embodiment.

Next, an operation of the refined oil degradation level measuring instrument 100 having such a configuration is described with reference to FIG. 4. First, the control signal is transmitted from the excitation light control unit 31 to irradiate the short pulsed excitation light R on the lubricant oil from the excitation light irradiation unit 1 (excitation light irradiation step S1). Then, the fluorescence Q generated in the lubricant oil by the irradiation is detected by the fluorescence intensity detection unit 2 to output the fluorescence intensity signal for indicating an intensity of the fluorescence Q (fluorescence intensity detection step S2).

Subsequently, the time lag characteristic calculation means can use, as a reference, the rise time of the control signal outputted by the excitation light control unit 31 to calculate a lag time from the fluorescence intensity signal received by the intensity signal reception unit (time lag characteristic calculation step S3).

After that, the degradation index value acquisition unit 35 refers to the correlation between the total base number and the lag time, which is acquired in advance, to acquire a total base number value from the measured lag time (degradation index value acquisition step S4), and the display unit 36 displays the total base number or a representative signal to the user (display step S5).

Thus, with a refined oil degradation level measuring instrument as described above, it is only necessary to provide the windows 1w and 2w in the oil tank T or other appropriate location to irradiate the excitation light R on the internal lubricant oil refined oil, and receive the fluorescence Q to perform calculation processing, and therefore, ultimately, by attaching such refined oil degradation level measuring instrument 100 to, for example, a car, a ship, or the like, a degradation level of lubricant oil in use can be monitored in real time without removing a sample of the lubricant oil from the lubrication system. Accordingly, the lubricant oil can be properly changed without waste with appropriate control panel displays to the user. Also, as an excitation light, a short pulsed light is used, and therefore even if the fluorescence intensity is weak, there is still an effect enabling measurements to be made with accuracy.

In addition, the present invention is not limited to the above-described embodiment. For example, the short pulsed light can be used as the excitation light; however, essentially, it is only necessary that an intensity of the excitation light varies with time. This is because the time lag characteristic is known by measuring the intensity variation of the fluorescence with respect to the intensity variation of the excitation light. Accordingly, as described above, an intensity of the excitation light may also be varied with a sine or triangle wave pattern. Also, it is possible that a frequency analysis of a time response wave of the fluorescence can be performed to relate a result of the analysis and the degradation index to each other. As the degradation index, a total acid number or neutralization number may be used. In addition to a lubricant oil, other oil products including an additive, for example, insulating oil or food oil can be measured in terms of a degradation level thereof.

The light source is not limited to an LED, but a semiconductor laser, a mercury lamp, or the like can also be used. Also, a wavelength of the excitation light may be changed depending on the type of refined oil, and a wavelength of the fluorescence to be acquired is also not limited to that in the above-described embodiment. Accordingly, the present invention can be variously modified without departing from the scope thereof.

REFERENCE SIGNS LIST

100: Refined oil degradation level measuring instrument
1: Excitation light irradiation unit
2: Fluorescence intensity detection unit
33: Time lag characteristic calculation unit
34: Correlation storage unit
35: Degradation index value acquisition unit
R: Excitation light
Q: Fluorescence Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. An oil degradation level measuring instrument to measure an oil degradation level of lubricant oil or insulating oil for one of an engine and a transformer comprising:
    an excitation light irradiation unit is controlled by a calculation device with a CPU configured to vary an intensity of excitation light to irradiate the excitation light on refined oil that is a measurement object;
    a fluorescence intensity detection unit is controlled by the CPU configured to detect an intensity of fluorescence that is generated in the refined oil irradiated with the excitation light;
    a time lag characteristic calculation unit is controlled by the CPU configured to calculate a time lag characteristic of a fluorescence intensity variation with respect to the intensity variation of the excitation light;
    a correlation storage unit preliminarily stores in a memory unit a correlation between a degradation index value indicating a degradation level of the refined oil and the time lag characteristic; and
    a degradation index value acquisition unit is controlled by the CPU configured to determine the correlation and to acquire the degradation index value from the memory unit based on the time lag characteristic calculated in the time lag characteristic calculation unit to determine the oil degradation level.

2. The oil degradation level measuring instrument according to claim 1, wherein
    the degradation index is a total base number.

3. The oil degradation level measuring instrument of claim 1, wherein the excitation light irradiation unit includes a laser light source, collimator lens, narrow band filter, and a collimator lens to direct excitation light through a light inlet window in an oil containing member of the refined oil.

4. The oil degradation level measuring instrument of claim 3, wherein the fluorescent intensity detection unit includes an optical sensor, a spectroscope, a collecting lens, a low pass filter and a collimator lens to receive fluorescence light through a light outlet window in an oil containing member of the refined oil.

5. The oil degradation level measuring instrument of claim 4 wherein the collimator lens of the excitation light irradiation unit is focused on a specific location of the refined oil and the collimator lens of the fluorescent intensity detection unit is also focused on the same specific location as the excitation light irradiation unit.

6. The oil degradation level measuring instrument of claim 5 includes the excitation light irradiation unit with a narrow band filter within a range of 350-380 nm and the fluorescent intensity detection unit includes a low pars filter within a range of 400-600 nm.

7. The oil degradation level measuring instrument of claim 6 wherein the excitation light irradiation unit generates pulsed light and the time lag characteristics is calculated from a rise time of a control signal generating the pulsed light.

8. The oil degradation level measuring instrument of claim 5 wherein an optical axis of the excitation light is offset from an optical axis of the detection unit and the light inlet window and the light outlet window are radially spaced on a circular oil containing member.

9. The oil degradation level measuring instrument of claim 1, wherein the fluorescent intensity detection unit includes an optical sensor, a spectroscope, a collecting lens, a low pass filter and a collimator lens to receive fluorescence light through a light outlet window in an oil containing tank of refined oil.

10. An oil degradation level measuring instrument to determine a current status degradation of lubricating oil being used in an internal combustion engine, comprising:
    a measurement quantity of lubrication oil within a lubrication system of the internal combustion engine;
    a source of excitation light of an intensity and wavelength controlled by a calculation device with a CPU configured to excite the measurement quantity of lubrication oil into a state of fluorescence;
    a detection unit is controlled by the CPU to measure an intensity of fluorescence light over a predetermined time period from the application of excitation light onto the quantity of lubrication oil;
    a time lag characteristic calculation unit is controlled by the CPU configured to calculate a time lag characteristic of a predetermined fluorescence intensity variation with respect to the application of the excitation light;
    a correlation storage unit that stores in a memory unit, a correlation between a degradation index value indicating a degradation level of the refined oil and the time lag characteristic;
    a degradation index value acquisition unit is controlled by the CPU to acquire the stored correlation of a degradation index value from the time lag characteristic calculated in the time lag characteristic calculation unit; and
    an output member to indicate a status signal representative of the current degradation status of the lubricating oil in the internal combustion engine.

11. An oil degradation level measuring method to measure an oil degradation level of lubricant oil or insulating oil for one of an engine and a transformer comprising:
    an excitation light irradiation step of varying an intensity of excitation light to irradiate the excitation light on refined oil that is a measurement object;
    a fluorescence intensity detection step of detecting an intensity of fluorescence that is generated in the refined oil irradiated with the excitation light;

a time lag characteristic calculation step of calculating a time lag characteristic of a fluorescence intensity variation with respect to the intensity variation of the excitation light; and a degradation index value acquisition step of referring to a preliminarily acquired correlation between a degradation index value indicating a degradation level of the refined oil and the time lag characteristic to acquire the degradation index value from the time lag characteristic calculated in the time lag characteristic calculation step.

12. The oil degradation level measuring method of claim 11, wherein a computer is configured to control the excitation light irradiation step and the fluorescence intensity detection step and to perform the calculation of the time lag characteristics of the time lag characteristic calculation step and to store the correlation of the degradation index value and time lag characteristics in a correlation storage unit to enable a determination of the degradation index value by the degradation index value acquisition step.

* * * * *